United States Patent [19]

Schock et al.

[11] Patent Number: 4,999,226

[45] Date of Patent: Mar. 12, 1991

[54] PHARMACEUTICAL COMPOSITIONS FOR PIPERIDINOALKANOL-IBUPROFEN COMBINATION

[75] Inventors: Herbert Schock, Cincinnati; David F. Long, Loveland; William R. Nadler, Cincinnati, all of Ohio

[73] Assignee: Merrell Dow Pharmaceuticals Inc., Cincinnati, Ohio

[21] Appl. No.: 344,183

[22] Filed: Apr. 27, 1989

Related U.S. Application Data

[63] Continuation of Ser. No. 200,817, Jun. 1, 1988, abandoned.

[51] Int. Cl.$^5$ ............................................. A61K 9/24
[52] U.S. Cl. .................................... 424/472; 424/471; 424/475; 424/480; 424/482
[58] Field of Search ............... 424/468, 475, 471, 472, 424/480, 482

[56] References Cited

U.S. PATENT DOCUMENTS 4,552,899 11/1985 Sunshine et al. ..................... 514/568
4,783,465 11/1988 Sunshine et al. ..................... 514/255
4,808,413 2/1989 Joshi et al. .......................... 424/458
4,882,167 11/1989 Jang .................................... 424/468

FOREIGN PATENT DOCUMENTS 0111144 10/1983 European Pat. Off. .

OTHER PUBLICATIONS

Abstract of Japanese Patent Application 137220, published Dec. 8, 1988.

Primary Examiner—Thurman K. Page
Attorney, Agent, or Firm—J. Michael Dixon

[57] ABSTRACT

The present invention is directed to a multi-layered tablet containing an ibuprofen layer, a piperidinoalkanol antihistamine layer, and a layer or layers containing conventional pharmaceutical excipients which is interspersed between the ibuprofen and piperidinoalkanol layer and serves to physically separate them. This tablet solves the problems associated with the physical and chemical incompatibilities between ibuprofen and the piperidinoalkanol antihistamines.

10 Claims, No Drawings

PHARMACEUTICAL COMPOSITIONS FOR PIPERIDINOALKANOL-IBUPROFEN COMBINATION

This is a continuation in part of Ser. No. 200,817, filed June 1, 1988 and now abandoned.

The present invention is directed to a pharmaceutical composition containing ibuprofen in combination with a piperidinoalkanol antihistamine.

As known to those skilled in the art, many of the products currently available for the treatment of the symptomatology associated with ailments such as the common cold, seasonal rhinitis, sinus headaches, sinusitis, etc., contain multiple therapeutic agents. Many of these products contain an antihistamine in combination with an analgesic. They can also contain a sympathomimetic decongestant. These combination products are convenient for the patient since they allow him to obtain relief from his numerous symptoms without taking multiple medications.

A variety of piperidinoalkanol derivatives possessing antihistaminic properties are disclosed in U.S. Pat. No(s). 3,878,217, 4,254,129, and 4,285,957. Specifically included within the scope of these patents is α-[4-(1,1-dimethylethyl)phenyl]-4-(hydroxydiphenylmethyl)-1-piperidinebutanol, known by its generic name as terfenadine. This agent is commercially available and has experienced widespread acceptance by consumers.

Recently attempts have been made to produce dosage forms which contain these piperidinoalkanol antihistamines in combination with other therapeutic agents.

One such attempt was to formulate a tablet containing the analgesic and antipyretic, ibuprofen, and the piperidinoalkanol antihistamine, α-[4-(1,1-dimethylethyl)phenyl]-4-(hydroxydiphenylmethyl)-1-piperidinebutanol. However, initial attempts failed. It was discovered that when a piperidinoalkanol such as α-[4-(1,1-dimethylethyl)phenyl]-4-(hydroxydiphenylmethyl)-1-piperidinebutanol is admixed directly with ibuprofen, a hardened mixture is formed rather than a flowable powder due to an incompatibility between these substances. Such a mixture is not amendable to further processing in order to form a pharmaceutical dosage form having acceptable bioavailability characteristics.

Further attempts were made to formulate such a dosage form by formulating a two-layered tablet wherein the piperidinoalkanol antihistamine and the ibuprofen were in separate layers. This formulation was not successful however. The presence of the ibuprofen caused the accelerated chemical degradation of the piperidinoalkanol. Attempts to retard this rate of degradation via anti-oxidants also failed.

Thus, it would be a valuable contribution to the art to develop a solid dosage form which contained both the analgesic and antipyretic, ibuprofen, and a piperidinoalkanol antihistamine such as α-[4-(1,1-dimethylethyl)phenyl]-4-(hydroxydiphenylmethyl)-1-piperidinebutanol.

In accordance with the present invention, it has been discovered that ibuprofen and a piperidinoalkanol antihistamine can be formulated into a solid dosage form by utilizing a multi-layered tablet wherein the piperidinoalkanol antihistamine containing layer and the ibuprofen layer are separated by at least one additional layer containing conventional pharmaceutical excipients. If desired, any of these layers can contain conventional cold, allergy and cough medications such as, for example, a sympathomimetic decongestant.

It is currently preferred that a three (3) layered tablet be utilized wherein a single middle layer containing only conventional pharmaceutical excipients serves as a barrier.

As used in this application, the term "piperidinoalkanol antihistamines" refers to those compounds described in U.S. Pat. No(s). 3,878,217, 4,254,129 and 4,285,957 and their pharmaceutically acceptable salts thereof, which are described as having antihistaminic activity. For purposes of the present invention, the preferred piperidinoalkanol antihistamine is α-[4-(1,1-dimethylethyl)phenyl]-4-(hydroxydiphenylmethyl)-1-piperidinebutanol. These piperidinoalkanols can be used according to the present invention as the free compound or as a pharmaceutically acceptable salt thereof as described in the above patents.

A therapeutically effective antihistaminic amount of a piperidinoalkanol is that amount which produces the desired antihistaminic response upon oral administration, and as known to those skilled in the art this amount can vary widely. Typically, the amount required to produce this result will vary from about 0.1 mg to about 140 mg. The preferred therapeutically effective antihistaminic amount will vary from about 20 mg to about 70 mg. The tablets will generally contain about 30 mg of the piperidinoalkanol antihistamine. In determining the therapeutically effective antihistaminic amount, a number of factors are considered, including but not limited to: the particular compound administered; the bioavailability characteristics of the pharmaceutical composition administered; the dose regimen selected; and other relevant circumstances.

As used in this application, the term "ibuprofen" refers to those nonsteroidal anti-inflammatory agents described in U.S. Pat. No. 3,228,831 as well as pharmaceutically acceptable salts thereof, with 2-(p-isobutylphenyl)propionic acid being most preferred. The quantity of ibuprofen required to produce the desired analgesic and antipyretic effect can vary widely as known to those skilled in the art and is affected by the same parameters described above for the appropriate dosage of the antihistamine. Generally the amount required to produce this effect will be within the range of from about 25 to about 400 mg and more preferably be within the range of from about 100 to about 300 mg. Generally though, the tablets will contain about 200 mg of ibuprofen.

As used in this application, the term "sympathomimetic decongestant" refers to those sympathomimetic agents which are therapeutically effective in providing relief of nasal congestion in a patient suffering therefrom. These agents include, but are not limited to, pseudoephedrine, phenylephrine, and phenylpropanolamine. As is well recognized and appreciated by those skilled in the art, these sympathomimetic drugs can be used according to the present invention as free amines or as pharmaceutically acceptable salts thereof.

A therapeutically effective decongestant amount of a sympathomimetic drug is that amount which produces the desired decongestant therapeutic response upon oral administration and can be readily determined by one skilled in the art by the use of conventional techniques and by observing results obtained under analogous circumstances. In determining the therapeutically effective amount, a number of factors are considered, including but not limited to: the particular compound administered; the bioavailability characteristics of the pharmaceutical composition administered; the dose regimen selected; and other relevant circumstances.

A therapeutically effective decongestant amount of a sympathomimetic drug will vary from about 1 mg to about 200 mg. Preferred amounts will vary from about 5 mg to about 150 mg. Generally the tablets will contain about 60 mg of pseudoephedrine.

The present invention is directed to the discovery of a pharmaceutical dosage form which solves the problem of the physical and chemical incompatibility between ibuprofen and the piperidinoalkanol antihistamines. As noted above, the solution is to formulate a multilayered tablet wherein the ibuprofen layer and the piperidinoalkanol antihistamine layers are physically separated by the presence of one or more intervening layers containing conventional pharmaceutical excipients, preferably one layer.

One of the layers will contain ibuprofen. This layer will typically comprise from about 30 to about 60 weight percent of total tablet weight, although it can vary widely as known to those skilled in the art. The quantity of ibuprofen contained within this layer can vary widely as discussed above. However, generally from about 100 mg to about 300 mg of ibuprofen will be contained in this layer, preferably about 200 mg. The ibuprofen will typically comprise from about 40 to about 80 weight percent of the ibuprofen layer.

The remaining 20–60 weight percent of the ibuprofen layer will contain conventional pharmaceutical excipients. These excipients typically include such items as a diluent which serves to increase the bulk of the tablet to a level suitable for conventional multi-layered tablet compression. Representative examples of suitable diluents include lactose, mannitol, crystalline sorbitol, starch, celluloses, microcrystalline cellulose, etc. Pregelatinized starch and microcrystalline cellulose are currently utilized.

The ibuprofen layer will also typically contain a lubricant that serves to improve the flow of the tablet granulation and prevents the adhesion of the tablet material to the surface of processing equipment such as tablet dies and tablet presses. Representative examples of suitable lubricants include talc, colloidal silicon dioxide, stearic acid, calcium stearate, zinc stearate, and magnesium stearate. Stearic acid, calcium stearate, talc and colloidal silicon dioxide are currently utilized.

The ibuprofen layer will also contain a disintegrating agent. The disintegrating agent serves to assist in the disintegration and breakup of the tablet following administration. Examples of suitable disintegrating agents include starch and starch derivatives such as, sodium starch glycolate, celluloses and cellulosic derivatives, cross-linked polyvinylpyrrolidone etc. Sodium starch glycolate is currently utilized.

Additionally, the ibuprofen layer will typically contain a binder which serves to impart a cohesiveness to the tablet formulation and insure tablet integrity following compression. Representative examples of suitable binders include povidone, starch, cellulose microcrystalline cellulose, sucrose, dextrose, acacia, sodium alginate, and carboxymethylcellulose. Povidone and pregelatinized starch are currently utilized.

If desired, the ibuprofen layer can also contain a preservative to inhibit contamination by microorganisms. Suitable preservatives include methyl and propyl parabens.

The amount of binder, diluent, preservative, disintegrant and lubricant utilized can vary widely as known to those skilled in the art. Typically though based upon the weight of the ibuprofen layer:
 (a) the diluent will be present in the quantity of from about 5 to about 50 weight percent;
 (b) the binder will be present in the quantity of from about 2 to about 15 weight percent;
 (c) the disintegrant will be present in the quantity of from about 0.5 to about 10 weight percent;
 (d) the lubricant will be present in the quantity of from about 0.1 to about 6 weight percent, and;
 (e) the preservative will be present in the quantity of from about 0 to about 1 weight percent.

Commercially available ibuprofen granulations are acceptable for use in the present invention. A preferred ibuprofen composition is available from Mallinckrodt Inc., under the tradename, DCI-63 ®.

In addition if desired, the ibuprofen layer can also contain additional therapeutic agents which are utilized to control the symptoms associated with the common cold and seasonal rhinitis. For example, it can also contain a sympathomimetic decongestant, such as, pseudoephedrine in the quantity of about 60 mg.

The middle layer or layers of the tablet serve to provide a physical barrier between the ibuprofen and the piperidinoalkanol antihistamine and thus serve to prevent the rapid degradation of the antihistamine. The quantity of excipients utilized in formulating this middle layer or layers can vary widely. Typically though, only a single layer will be utilized to serve as a physical barrier between the ibuprofen and piperidinoalkanol antihistamine. The middle layer or layers will typically comprise from about 5 to about 40 weight percent of the total tablet weight, more preferably from about 5 to about 30 weight percent of the total tablet weight, and most preferably from about 10 to about 15 weight percent of the total tablet weight. The middle layer or layers can be manufactured from a variety of conventional pharmaceutical excipients, and typically will contain a diluent in combination with a binder. If desired a lubricant can be added to facilitate compression. Any of the diluents and binders described above are suitable for use in this layer or layers. Microcrystalline cellulose is currently utilized which serves to act as both a binder and a diluent. If desired, conventional therapeutic agents such as a sympathomimetic decongestant can be incorporated into this layer or layers without affecting the stability of the piperidinoalkanol antihistamine.

Another layer of the tablet contains the piperidinoalkanol antihistamine. This layer will generally comprise from about 30 to about 60 weight percent of total tablet weight. As noted previously, it is preferred that the piperidinoalkanol antihistamine be α-[4-(1,1-dimethylethyl)phenyl]-4-(hydroxydiphenylmethyl)-1-piperidinebutanol. The quantity of antihistamine can vary as described above, however typically it will contain about 30 mg.

In a preferred embodiment of the present invention, this layer will also contain a sympathomimetic decongestant. Currently about 60 mg of pseudoephedrine is incorporated into this layer. Other sympathomimetic decongestants are equally suitable.

This layer will also contain pharmaceutical excipients such as, diluents, binders, and lubricants. Since the piperidinoalkanol antihistamines are only sparingly soluble in water, it is preferred that the layer containing the piperidinoalkanol contain the disintegrating agent, calcium carbonate, in a quantity of from about from about 2 to about 50 weight percent based upon the weight of the piperidinoalkanol layer, and more preferably from about 10 to 20 weight percent. It is readily apparent to one skilled in the art that the calcium carbonate may be replaced in whole or in part by other pharmaceutically acceptable carbonate or bicarbonate salts, such as sodium bicarbonate. Calcium carbonate is preferred because of its advantageous handling characteristics (i.e., less sensitive to high humidity). Other disintegrating agents such as sodium starch glycolate can also be incorporated into the composition.

It is also preferred that a solubilizing agent be incorporated into the piperidinoalkanol layer. This solubilizing agent is generally a non-ionic or cationic surfactant, present in a quantity of from about 0.1 to about 6 weight percent based upon the weight of the piperidinoalkanol layer, and more preferably from about 1 to about 4 weight percent.

As used in this application, the term "nonionic surfactant" means and includes pharmaceutically acceptable nonionic surfactants known in the art of pharmaceutical science, including various nonionic compounds containing relatively hydrophilic and relatively hydrophobic regions. Typically these surfactants are alkoxylates of hydrophobic amines, acids or alcohols. For example, the term "pharmaceutically acceptable nonionic surfactants" is contemplated to include the following agents within its scope: various long chain fatty acid esters of polyoxyethylene sorbitan, such as Polysorbate 80 (also known as Tween 80 ®); various poloxamers or pluronics, such as Pluronic-F68 ®, polyethylene glycols of various average molecular weights, and derivatives thereof such as polyoxyethylene fatty acid esters (for example polyethylene glycol monostearate); or mixtures thereof. The preferred nonionic surfactants in the pharmaceutical composition of the present invention are polyoxyethylene sorbitan fatty acid esters and polyethylene glycol (average molecular weight about 4000 to about 9000). Polysorbate 80 and polyethylene glycol (average molecular weight about 8000) are especially preferred.

As used in this application, the term "cationic surfactant" means and includes various ionic compounds with a positively charged ionic species containing relatively hydrophobic regions. Typically these surfactants are quaternary ammonium salts, such as for example, cetylpyridinium chloride, cetyl trimethyl ammonium bromide and benzalkonium chloride. The preferred cationic surfactant for purposes of the present invention is cetylpyridinium chloride.

The piperidinoalkanol layer will also typically contain a diluent. Representative examples of suitable diluents include microcrystalline cellulose, starch, lactose, mannitol, crystalline sorbitol, celluloses, etc. Pregelatinized starch and microcrystalline cellulose are currently utilized. The diluent is typically present in a quantity of from about 25 weight percent to about 75 weight percent based upon weight of the piperidinoalkanol layer.

This layer will also typically contain a binding agent in the quantity of from about 1 to about 20 weight percent based upon the weight of the piperidinoalkanol layer. Suitable binding agents include povidone, starch, microcrystalline cellulose, sucrose, dextrose, acacia, sodium alginate, and carboxymethylcellulose. Pregelatinized starch and microcrystalline cellulose are currently utilized.

It will also contain a lubricant in the quantity of from about 1 to about 20 weight percent based upon the weight of the piperidinoalkanol layer. Representative examples of suitable lubricants include talc, colloidal silicon dioxide, stearic acid, calcium stearate, zinc stearate, and magnesium stearate. Talc, magnesium stearate and colloidal silicon dioxide are currently utilized.

It is of course understood that tablets produced according to the present invention can be film or sugar coated using standard ingredients and procedures commonly used and well known in the pharmaceutical sciences. It is contemplated that tablets so coated are within the scope of the present invention.

The ingredients of the pharmaceutical composition of the present invention are brought together into a dosage form for oral administration according to standard practices and procedures well known in the pharmaceutical sciences using conventional formulation and manufacturing techniques. The terfenadine layer is wet granulated, dried, and blended with lubricants according to techniques known in the art. The commercially available ibuprofen granulation is blended with lubricants. It is currently preferred that the triple layered tablet be manufactured utilizing a triple layer tablet press.

The pharmaceutical composition of the present invention demonstrates acceptable in vitro dissolution characteristics which indicate that the composition provides efficient bioavailability of the therapeutically active ingredients in an immediate release manner. According to the present invention, it is understood that the term "immediate release" contemplates a biopharmaceutical concept indicating the absence of delayed release characteristics.

The dosage range of these tablets can vary widely depending upon the amount of active ingredient contained within the dosage form, the particular medications incorporated into the dosage form, the patient, the severity of the patient's symptoms, etc. Typically though, the dose will be one or two tablets administered from 2 to 4 times daily.

As used in this application, the term "patients" refers to a warm blooded mammal such as, for example, rabbits, mice, rats, guinea pigs, chimpanzees, humans, etc.

The following example is illustrative of preferred embodiments of the present invention and are not intended to limit the scope of the present invention in any way.

EXAMPLE I

The following table illustrates the composition of the currently preferred pharmaceutical composition of the present invention:

TABLE I

|  | Mg/Tablet |
|---|---|
| Ibuprofen Layer | |
| Directly Compressible Ibuprofen (63 wt %)[1] | 328.0 |
| Sodium Starch Glycolate | 6.0 |
| Microcrystalline Cellulose | 7.5 |
| Talc | 5.0 |
| Colloidal Silicon Dioxide | 5.0 |
| SUB-TOTAL | 351.5 mg |
| Inert Layer | |
| Microcrystalline Cellulose (PH 102) | 100.0 mg |
| Terfenadine-Pseudoephedrine Layer | |
| Pseudoephedrine.HCl | 60.0 |
| Terfenadine | 30.0 |
| Calcium Carbonate | 42.0 |
| Microcrystalline Cellulose | 115.5 |
| Polysorbate 80 | 5.3 |

TABLE I-continued

| | Mg/Tablet |
|---|---|
| Starch 1500 | 60.0 |
| Sodium Starch Glycolate | 6.0 |
| Talc | 5.0 |
| Colloidal Silicon Dioxide | 5.0 |
| SUB-TOTAL | 328.8 mg |
| Film Coating | |
| Hydroxypropyl Methylcellulose 2910 | 13.3 |
| Myvacet 9-40 ® | 1.3 |
| Opaspray K-1-2483 ® | 6.0 (2.4 solids) |
| SUB-TOTAL (SOLIDS) | 17.0 mg (of added solids) |

[1]Available under the tade name, DCl-63 ® from Mallinckrodt, Inc.

METHOD OF MANUFACTURE

This tablet was manufactured in the following manner:

a. Terfenadine/pseudoephedrine layer

In a high intensity mixer, 2.457 kg terfenadine, 4.913 kg pseudoephedrine HCl, 3.439 kg calcium carbonate, 8.844 kg microcrystalline cellulose, and 4.913 kg starch were combined and mixed thoroughly. A granulation solution (consisting of 0.434 kg Polysorbate 80 dissolved in 8 kg purified water) was prepared and slowly add to the powder blend with mixing. Mixing continued until granules were formed. The granulation can be wet screened if necessary. The granulation was dried to a moisture level of approximately 2% (Loss on Drying Method). The dried granulation was milled using a Fitzmill equipped with a 0014 screen (14 mesh).

To the sized granulation, was added 0.614 kg microcrystalline cellulose PH 102, and after screening, the following: 0.491 kg starch glycolate sodium, 0.409 kg silicon dioxide, and 0.409 kg of talc. The resulting mixture was blended in a V-Blender until a suitably mixed lubricated granulation was achieved.

b. Inert Layer

Microcrystalline cellulose PH 102 was used unprocessed.

c. Ibuprofen Layer

To 26.859 kg Ibuprofen DCI 63% ®, was added 0.614 kg microcrystalline cellulose PH 102, and after screening, the following: 0.491 kg starch glycolate sodium, 0.409 kg silicon dioxide, and 0.409 kg talc. In a V-Blender, the mixture was blended until a suitably mixed lubricated granulation was achieved.

d. Tablet Compression

Either the terfenadine/pseudoephedrine HCl layer or the ibuprofen layer may be utilized as the first layer of the tablet. For this example, the terfenadine/pseudoephedrine layer was compressed first.

A tablet press capable of compressing multiple layers was utilized to compress the tablets. The terfenadine pseudoephedrine HCl granulation was fed to the tablet press and compacts with an average target weight of about 330 mg were compressed. About 100 mg of the inert layer was then fed on top of the compact of layer one and then compressed. Finally, an average of about 350 mg of the ibuprofen granulation was fed on top of compressed layers one and two, and subjected to further compression.

Approximately 81,886 tablets were compressed. The average tablet weight was 780 mg, thickness was 6-7 mm, hardness was 8-20 kg (Schleuniger), and friability was not more than 1%.

e. Tablet Film Coating

The film coating was prepared by mixing 1.92 kg of ethyl alcohol (95 weight percent) with 1.60 kg of purified water. 0.310 kg of HPMC 2910 was added to this mixture with mixing, followed by 0.3 kg of acetylated monoglycerides (Myvacet 9-40 ®) with further mixing. Finally 0.140 kg of Opraspray ® was added and mixed well to disperse the color suspension.

7.0 kg of the compressed tablets were placed in a suitable 24" coating pan. The tablets were tumbled in the coating pan while the coating preparation was applied to the tablets via an atomized spraying system having an inlet drying temperature of about 120° F. The coating preparation was applied until an approximately 2% gain in tablet weight was achieved.

What is claimed is:

1. A multi-layered pharmaceutical tablet in a solid unit dosage form comprising:
    (a) a layer comprising a therapeutically effective analgesic and antipyretic amount of ibuprofen or a pharmaceutically acceptable salt thereof, in admixture with pharmaceutically acceptable excipients;
    (b) a layer comprising a therapeutically effective antihistaminic amount of a piperidinoalkanol or a pharmaceutically acceptable salt thereof, in admixture with pharmaceutically acceptable excipients, and;
    (c) a layer comprising a pharmaceutically inert excipient, which is interspersed between said ibuprofen containing layer and said piperidinoalkanol containing layer in order to provide a barrier layer there between.

2. The composition of claim 1, wherein said barrier layer is present in quantity of from about 5 to about 40 weight percent based upon the total weight of the tablet.

3. The composition of claim 1 wherein said barrier layer is present in a quantity of from about 5 to about 30 weight percent based upon the total weight of the tablet.

4. The composition of claim 1 wherein said barrier layer is present in a quantity of from about 10 to about 15 weight percent based upon the total weight of the tablet.

5. The composition of claim 4 wherein said barrier layer is composed of a diluent and binder.

6. The composition of claim 5 wherein said binder and diluent is microcrystalline cellulose.

7. The composition of claim 1, wherein at least one of the layers contains a sympathomimetic decongestant agent.

8. The composition of claim 5 wherein said piperidinoalkanol antihistamine layer further contains a sympathomimetic decongestant.

9. The composition of claim 8 wherein said sympathomimetic decongestant agent is pseudoephedrine, said piperidinoalkanol is α-[4-(1,1-dimethylethyl)phenyl]-4-(hydroxydiphenylmethyl)-1-piperidinebutanol, said ibuprofen is 2-(p-isobutyl-phenyl)propionic acid, and the pharmaceutically acceptable salts of said compounds.

10. The composition of claim 9 wherein:
    (a) said ibuprofen is present in the quantity of from about 100 mg to about 300 mg;
    (b) said pseudoephedrine is present in the quantity of from about 15 mg to about 60 mg.
    α-[4-(1,1-dimethylethyl)phenyl]-4-(hydroxydiphenylmethyl)-1-piperidinebutanol is present in the quantity of from about 15 to about 60 mg.

* * * * *